Nov. 8, 1955 E. G. FISHER Plant Pat. 1,433
ROSE PLANT
Filed Jan. 28, 1955
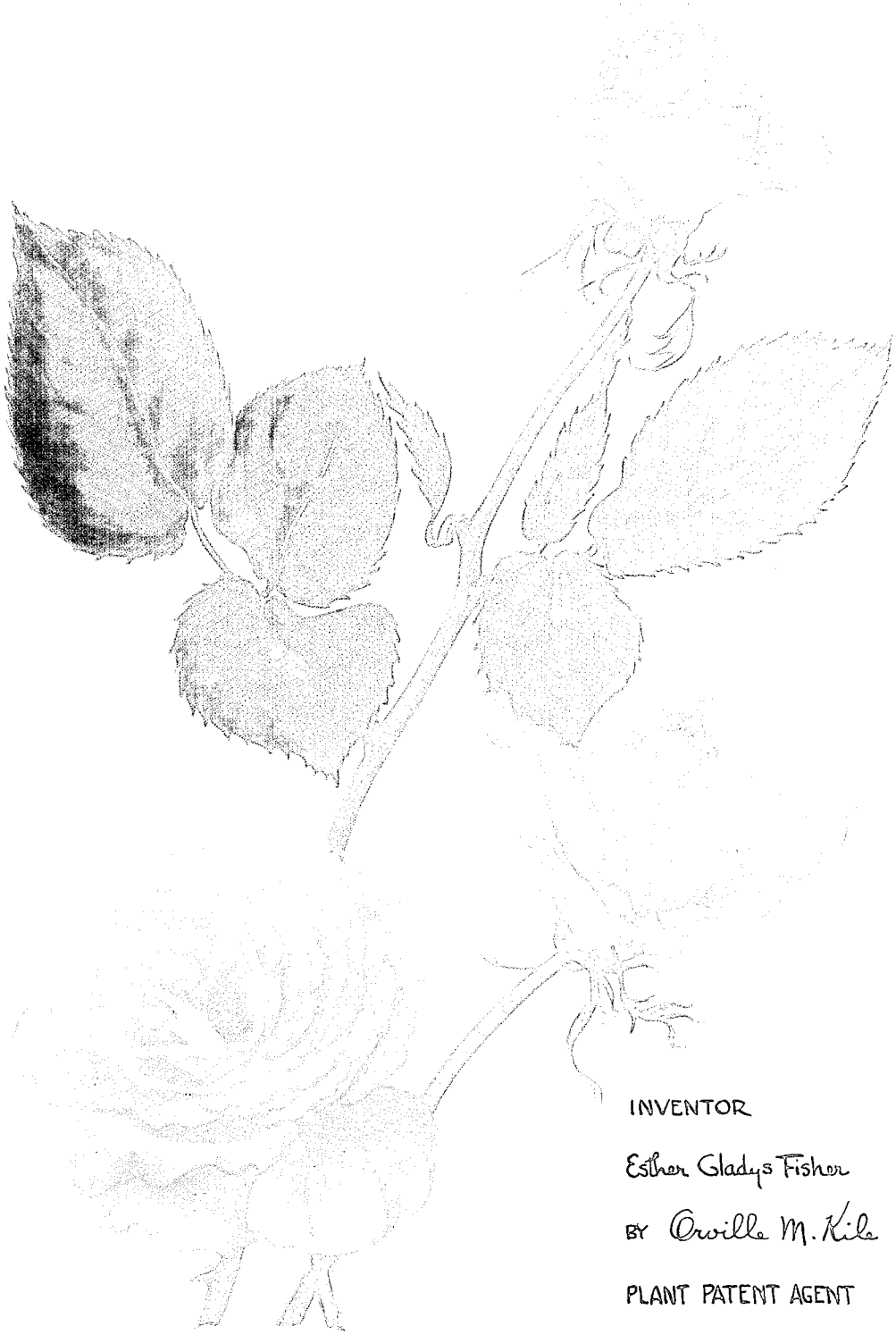
INVENTOR
Esther Gladys Fisher
BY Orville M. Kile
PLANT PATENT AGENT United States Patent Office Plant Pat. 1,433
Patented Nov. 8, 1955

1,433

ROSE PLANT

Esther Gladys Fisher, Woburn, Mass., assignor to Arnold-Fisher Company, Woburn, Mass.

Application January 28, 1955, Serial No. 484,861

1 Claim. (Cl. 47—61)

My present invention relates to a new and distinct variety of hybrid tea rose plant of the novelty type, being a combination of a strong-growing plant and a flower of a color new to roses and with intense fragrance.

This new variety is the result of definite breeding efforts made by me. Its male parent was the variety Peace (Plant Patent No. 591) and an unnamed seedling as the female parent—the latter coming from a strain similar to the parentage of Morning Mist (Plant Patent No. 999).

Asexual reproduction has been accomplished by budding and grafting work done by me in greenhouses, located in Woburn, Massachusetts.

The variety is a strong and fast grower and produces good bushes. It is also a prolific producer of blooms on strong stems. The most outstanding characteristics of the variety are its dark glossy foliage and its flower of true lavender color which is also very fragrant.

Accompanying illustrations show three typical specimens of the bloom in varying stages of opening, together with portions of the stems and foliage.

Color plate references in the following detailed description indicate Ridgway's Color Standards and Nomenclature, while other color terminology indicates the ordinary dictionary meaning of the term.

*The plant*

Growth habit: Strong and fast grower, the bush usually attaining a height of about 4 feet. It is primarily a greenhouse rose but also grows well as a garden rose.

Blooming habit: Prolific bloomer throughout the year when greenhouse grown.

Stem: Strong but not heavy. Considerably lighter in color than the upper surface of the foliage, being approximately Biscay Green (Pl. XVII). Very few thorns present on stem.

Foliage:

*Type.*—Pinnately compound, with 3 to 5 leaflets.

*Quantity.*—Abundant.

*Size.*—Large. Terminal leaflets on a typical specimen average approximately 3 inches long and 2 inches wide.

*Shape.*—Broad oval with rounded bases. Terminal leaflet has acuminate apex, while lateral ones are usually merely pointed. Edge sharply serrated.

*Texture.*—Leathery but thin.

*Rachis.*—Slender. Grooved and usually red-tinged above; under surface light green and smooth except for an occasional small thorn.

*Stipules.*—Prominent; long-pointed.

*Color.*—Dark green on upper surface, approximately Dark Dull Yellow Green (Plate XXXII) in shade, but with a very glossy aspect. Under surface approximately Light Elm Green (Plate XVII).

*The flower*

Bud:

*Size.*—Medium; 1¼ inch long just before unfolding.

*Form.*—Long and somewhat pointed. High-centered as it opens.

*Color.*—Light Vinaceous-Lilac with Vinaceous-Lilac (both Plate XLIV) in the depths of the opening bud.

*Sepals.*—Long; slightly foliaceous; reflex early, later clasping stem.

*Calyx.*—Small; smooth; same color as stem.

*Peduncle.*—Relatively short—two to four inches; slender but very strong.

Bloom:

*Borne.*—Singly on medium to long stems.

*Size.*—Medium, measuring up to 3½ inches in diameter when fully expanded.

*Form.*—High-centered at first, later becoming cup-shaped, and finally petals reflexing slightly. Usually the large center of contrasting yellow stamens becomes visible in the cup-shape stage.

*Petalage.*—Average 30 to 35 petals.

*Scent.*—Intense, pleasing fragrance.

Petals:

*Texture.*—Delicate and silky.

*Shape.*—Approximately round, with slight point at tip. Usually the petals are slightly wavy, giving them the appearance of having slightly pointed edges.

*Longevity.*—Usual.

*Color.*—Pure Light Vinaceous-Lilac with some Vinaceous-Lilac in the depths of the opening rose. As the rose ages, it becomes a little lighter, the petal edges then being approximately Pale Vinaceous-Lilac. (All Plate XLIV.)

Reproductive organs:

*Pistils.*—Bunched in center of flower. Styles short; yellow, approximately Buff Yellow (Plate IV). Stigmas same color as styles.

*Stamens.*—Surround pistils. Filaments light cream color; curved inward; arise above pistils. Anthers medium-sized; approximately Light Orange Yellow (Plate III), later turning brown.

Having thus disclosed my invention, I claim:

The new and distinct variety of hybrid tea rose plant, substantially as herein shown and described, characterized particularly by its strong, rapid growth and its large, soft, dark green foliage; in combination with the intense fragrance and vinaceous-lilac color of its bloom.

No references cited.